United States Patent
White

(10) Patent No.: US 10,228,127 B2
(45) Date of Patent: Mar. 12, 2019

(54) HEAT ISOLATING TORCH

(71) Applicant: Lamplight Farms Incorporated, Menomonee Falls, WI (US)

(72) Inventor: Ron White, North Prairie, WI (US)

(73) Assignee: Lamplight Farms Incorporated, Menomonee Falls, WI (US)

( * ) Notice: Subject to any disclaimer, the term of this patent is extended or adjusted under 35 U.S.C. 154(b) by 0 days.

(21) Appl. No.: 15/209,523

(22) Filed: Jul. 13, 2016

(65) Prior Publication Data

US 2016/0320053 A1     Nov. 3, 2016

Related U.S. Application Data

(63) Continuation of application No. 13/762,999, filed on Feb. 8, 2013, now Pat. No. 9,416,962.

(51) Int. Cl.

| | |
|---|---|
| *F23D 3/18* | (2006.01) |
| *F23D 3/04* | (2006.01) |
| *F23D 14/76* | (2006.01) |
| *F21V 37/00* | (2006.01) |
| *F21S 13/12* | (2006.01) |
| *F23D 3/24* | (2006.01) |
| *F23D 3/26* | (2006.01) |
| *F23D 3/02* | (2006.01) |
| *A61L 9/03* | (2006.01) |
| *F21V 25/00* | (2006.01) |
| *F21V 29/15* | (2015.01) |

(52) U.S. Cl.
CPC .............. *F23D 3/04* (2013.01); *F21S 13/12* (2013.01); *F21V 37/0004* (2013.01); *F23D 3/24* (2013.01); *F23D 3/26* (2013.01); *F23D 14/76* (2013.01); *A61L 9/037* (2013.01); *F21V 25/00* (2013.01); *F21V 29/15* (2015.01); *F21V 37/0016* (2013.01); *F21V 37/0058* (2013.01)

(58) Field of Classification Search
CPC .................................. F21V 37/00; F23D 3/18
USPC ......................................................... D26/6–8
See application file for complete search history.

(56) References Cited

U.S. PATENT DOCUMENTS

| | | |
|---|---|---|
| 203,043 A | 4/1878 | Hillegass |
| 613,188 A | 10/1898 | Cadwallader et al. |
| 1,554,130 A | 9/1925 | Sargeant |
| 1,705,877 A | 3/1929 | Ramsey |
| 2,122,624 A | 7/1938 | Sauer |
| 2,217,970 A | 10/1940 | Shearman et al. |

(Continued)

FOREIGN PATENT DOCUMENTS

| | | |
|---|---|---|
| CA | 2675817 | 10/2010 |
| CN | 2670364 | 1/2005 |

(Continued)

OTHER PUBLICATIONS

DE 202004014016 U1—English machine translation.*

(Continued)

*Primary Examiner* — Jorge Pereiro

(74) *Attorney, Agent, or Firm* — David G. Woodral; Gable Gotwals

(57) ABSTRACT

A device with a flame bowl for a torch having a torch body containing a fuel supply. A fitting attaches to the flame bowl for interfacing with the fuel supply. A perforated support affixes the flame bowl in an elevated position relative to a portion of the torch body.

13 Claims, 14 Drawing Sheets

(56) References Cited

U.S. PATENT DOCUMENTS

| | | |
|---|---|---|
| 2,684,182 A | 7/1954 | Gey |
| 2,744,809 A | 5/1956 | Falligant |
| 2,836,043 A | 5/1958 | Spethmann |
| 3,270,192 A | 8/1966 | Watson |
| 3,364,704 A | 1/1968 | Bernstein |
| D262,999 S | 2/1982 | Spencer |
| 4,477,247 A | 10/1984 | Kumasaka |
| D286,682 S | 11/1986 | Greenlee |
| 5,083,916 A | 1/1992 | Glennon et al. |
| 5,101,328 A | 3/1992 | Hai |
| 5,205,730 A | 4/1993 | Capdeville |
| 5,807,093 A | 9/1998 | Tendick, Sr. |
| D404,507 S | 1/1999 | Palmer et al. |
| 5,902,101 A | 5/1999 | Palmer et al. |
| 5,938,430 A | 8/1999 | Majerowski |
| D433,763 S | 11/2000 | Donato |
| 6,231,336 B1 | 5/2001 | Chen |
| 6,345,978 B1 | 2/2002 | Lu |
| D456,917 S * | 5/2002 | Kumar .................. D26/114 |
| 6,428,311 B1 | 8/2002 | Bernardo |
| D470,962 S | 2/2003 | Chen |
| 6,514,070 B2 | 2/2003 | Lu |
| D473,669 S | 4/2003 | Hille et al. |
| 6,565,012 B1 * | 5/2003 | Zaragoza ................ A61L 9/12 237/57 |
| 6,612,720 B1 | 9/2003 | Beadle |
| 6,663,258 B1 | 12/2003 | Kanter |
| D495,079 S | 8/2004 | Mullen |
| 7,156,653 B1 | 1/2007 | Demars |
| D575,893 S | 8/2008 | Castellucci et al. |
| D589,188 S | 3/2009 | Sabernig |
| D591,896 S | 5/2009 | Plonski et al. |
| D611,637 S | 3/2010 | Sabernig |
| D611,640 S | 3/2010 | Sabernig |
| D625,850 S | 10/2010 | Lu |
| D659,871 S | 5/2012 | Lee et al. |
| 2001/0053504 A1 | 12/2001 | Lu |
| 2006/0147864 A1 | 7/2006 | Donley |
| 2006/0199129 A1 | 9/2006 | Konkle, Jr. |
| 2006/0251997 A1 * | 11/2006 | Schulte ............... A01M 1/2088 431/343 |
| 2007/0020572 A1 | 1/2007 | Furner et al. |
| 2007/0169409 A1 | 7/2007 | Chang |
| 2009/0068608 A1 | 3/2009 | Hansen |
| 2009/0220904 A1 | 9/2009 | Masterson et al. |
| 2010/0112503 A1 * | 5/2010 | Masterson .......... F21V 37/0062 431/301 |
| 2010/0255436 A1 | 10/2010 | Lu |
| 2011/0097676 A1 | 4/2011 | Masterson et al. |

FOREIGN PATENT DOCUMENTS

| | | | |
|---|---|---|---|
| CN | 201014219 | 1/2008 | |
| CN | 201348155 | 11/2009 | |
| DE | 202004014016 U1 * | 11/2004 | ............. F21V 25/00 |
| FR | 2745362 | 8/1997 | |
| WO | WO03106895 | 12/2003 | |

OTHER PUBLICATIONS

Pipe-Line Denmark, "Elipse Advanced Burning Control". Publication unknown, admitted prior art.

European Patent Office, "Extended European Patent Search for European Patent Application No. 13165624.1", dated Jul. 25, 2013, Published in: NL.

Pipe-Line Denmark, "The Torch Master Brochure", Publisher: http://www.pipe-line.dk/pdf/English2007WEB.pdf. Publication unknown, admitted prior art.

* cited by examiner

HEAT ISOLATING TORCH

CROSS REFERENCE TO RELATED APPLICATIONS

This is a continuation of co-pending U.S. patent application Ser. No. 13/762,999, entitled "HEAT ISOLATING TORCH" filed on Feb. 8, 2013 which is a Continuation-in-Part of U.S. patent application Ser. No. 13/460,390 entitled "HEAT ISOLATING TORCH," filed Apr. 30, 2012 (now U.S. Pat. No. 9,115,884), the contents of which are hereby incorporated by reference.

FIELD OF THE INVENTION

This disclosure relates to liquid fueled torches in general and, more particularly, to a liquid fueled torch that isolates heated components from a user.

BACKGROUND OF THE INVENTION

Liquid fueled torches are utilized for a number of purposes such as lighting, decoration, and pest repellence. Some fuel and torch combinations operate at extremely high temperatures. This is particularly so where a large flame presence is desired, or where high temperatures are utilized to disperse repellants or other useful substances. For safety reasons, torches are rarely left unattended; and some users will want to place torches into storage as soon as possible after use. Sometimes it may also be desirable to relocate a torch that is operating, or has recently been operating.

What is needed is a system and method for addressing the above, and related, issues.

SUMMARY OF THE INVENTION

The invention of the present disclosure, in one aspect thereof, comprises a device having a flame bowl for a torch having a torch body containing a fuel supply. A fitting is attached to the flame bowl for interfacing with the fuel supply. A perforated support affixes the flame bowl in an elevated position relative to a portion of the torch body.

In some embodiments, the support is provided with radiative fins. The perforations may comprise louvers. A first shroud may circumscribe the flame bowl. Some embodiments also include a second shroud circumscribing the first shroud, the flame bowl, and the perforated support. The perforated support may have a substantially frustroconical shape. The perforated support may have a smaller radius proximate the flame bowl and a larger radius spaced apart from the flame bowl.

Some embodiments further comprise a torch top having a recess in an upper surface thereof. The recess may contain the flame bowl. The recess may comprise a sidewall descending from the upper surface and affixing to the perforated support. A shroud may circumscribe the flame bowl at a level proximate the upper surface.

The invention of the present disclosure, in another aspect thereof, comprises a device having a flame bowl circumscribed by a first, inner shroud. The device has a shell having a second, outer shroud on an upper portion thereof, the outer shroud circumscribing at least a portion of the first shroud. A perforated support maintains the flame bowl and the first shroud in a fixed relationship with respect to the outer shroud. A third, intermediate shroud circumscribes the perforated support and interposes the first and second shrouds.

The perforated support may have a shape that is substantially frustroconical with a lower end wider than an upper end. The device may include a lip in the shell that supports the perforated support in a predetermined position inside the shell. The first, second, and third shrouds may have an angled profile with an upper rim and a lower rim. A fuel container fitting may be attached to the flame bowl.

The invention of the present disclosure, in another aspect thereof, comprises a device with a torch top having a recess in an upper surface thereof, a flame bowl having a wick holder, and a perforated support that retains the flame bowl at a fixed position within the recess.

In some embodiments, the recess further comprises a sidewall extending downward from the upper surface to connect with the perforated support within the recess. A first shroud may attach to the flame bowl and circumscribe the wick holder. A second shroud may be situated at least partially within the recess and circumscribe the first shroud. A fuel container fitting may be affixed to the flame bowl and be at least partially circumscribed by the perforated support.

In some embodiments, the perforated shroud has a substantially fustroconical shape. The perforated support may expand in diameter into the recess. A lower portion of the sidewall may extend inwardly to attach to the perforated support.

DETAILED DESCRIPTION OF THE PREFERRED EMBODIMENTS

Figure 1:
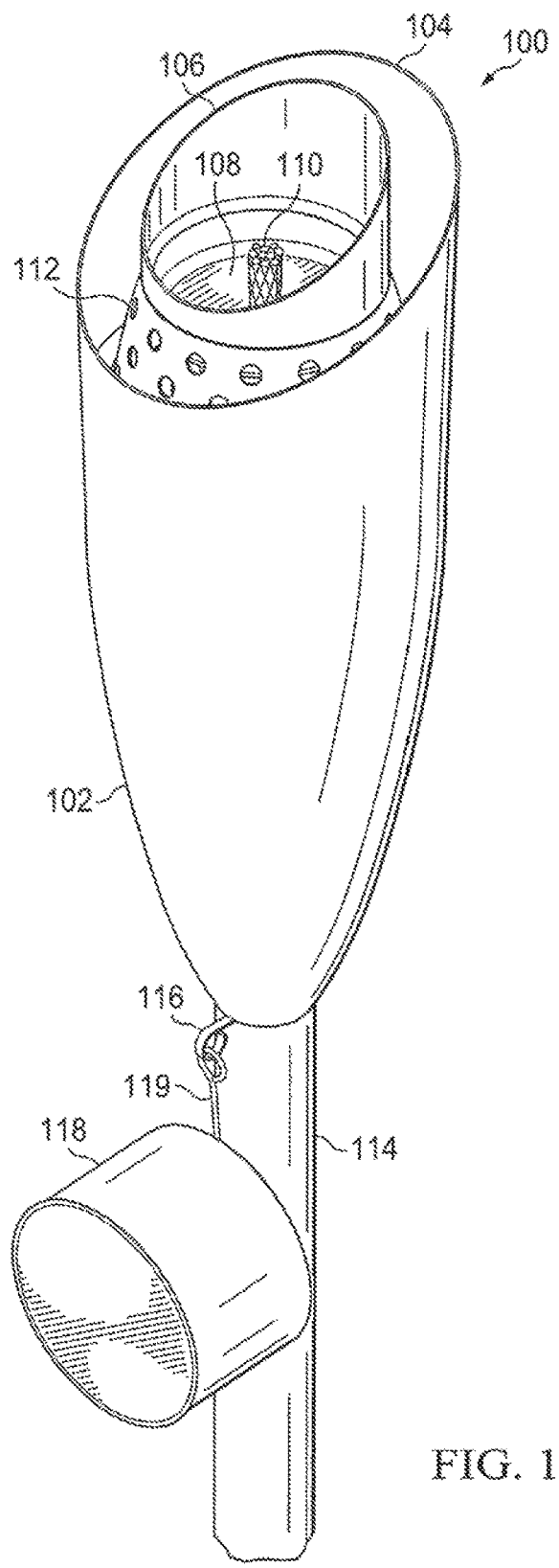
FIG. 1 is a front perspective view of one embodiment of a heat isolating torch according to the present disclosure.

Referring now to FIG. 1, a front perspective view of one embodiment of a heat isolating torch according to the present disclosure is shown. The torch 100 is referred to herein as being "heat isolating" due to the features described herein that reduce the temperature of the torch 100 at locations where a user would be likely to grasp or touch the torch 100. The torch 100 has a body 102 that may be made from steel or another metal. In some embodiments, the surface of the body 102 may comprise rolled steel and have a brushed or stainless appearance. Other embodiments may have a body 102 comprising a polymer or another suitable material. The body 102 may be cylindrical with a tapered lower portion. The body 102 also comprises an outer shroud 104. In some embodiments, the shroud 104 will be a continuous portion of the body 102.

The torch 100 may also comprise an inner shroud 106 surrounding a flame bowl 108. The flame bowl 108 and/or an interior portion of the inner shroud 106 may be texturized to promote a large and/or decorative flame from the wick 110. The inner shroud 106 and the flame bowl 108 may comprise steel or another heat resistant material. The wick 110 may be a durable fiberglass wick or another wick capable of withstanding high temperatures without being consumed.

A support 112 offsets the inner shroud 106 and flame bowl 108 from the body 102 of the torch 100. In some embodiments, the support 112 may be perforated in order to allow dissipation of heat as well as limiting heat that can be transferred from the inner shroud 106 and/or flame bowl 108 to the torch body 102. In some embodiments, the support 112 will comprise a heat resistant steel, and may comprise the same material as the flame bowl 108 and/or inner shroud 106.

The torch body 102 may have an attached pole 114 that may be placed in the ground or otherwise affixed to a secure surface. The pole 114 may be wooden, metal, plastic, or made from another material. In other embodiments, the torch 100 may be freestanding or configured for placement on a tabletop. A hook 116 may be provided on the body 102, the pole 114, or at the conjunction of the two, as shown. In the present embodiment, the hook 116 is configured to retain a snuffer cap 118, via an attached handle 119, when the cap 118 is not in use.

Figure 2:
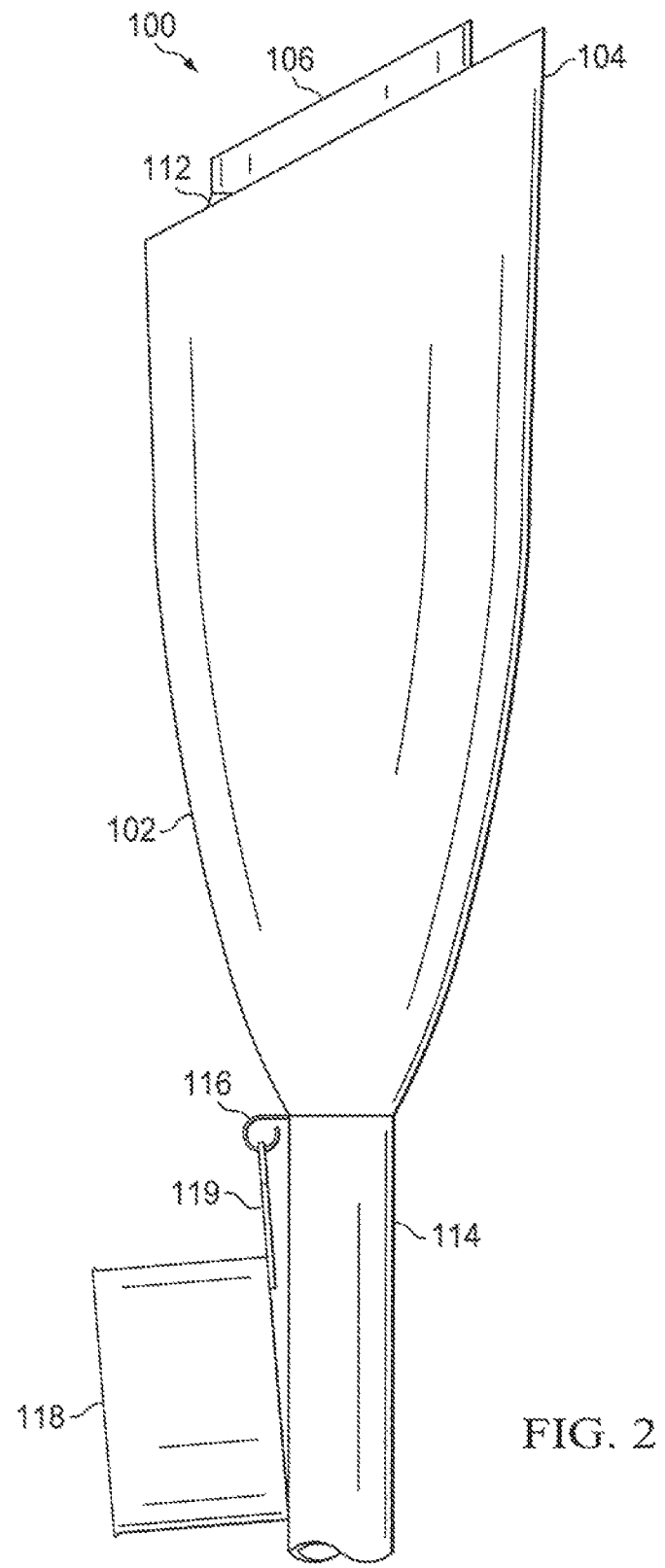
FIG. 2 is a side view of the torch of FIG. 1.

Referring now to FIG. 2, a side view of the torch 100 of FIG. 1 is shown. From the viewpoint of FIG. 2, it can be seen that the outer shroud 104 and inner shroud 106 are cut at an angle in the present embodiment. This configuration is decorative in some embodiments, but in other embodiments the configuration will allow for additional heat isolation and/or dispersion. It can also be seen that, in the present embodiment, the inner shroud 106 is raised only slightly above the level of the outer shroud 104.

Figure 3:
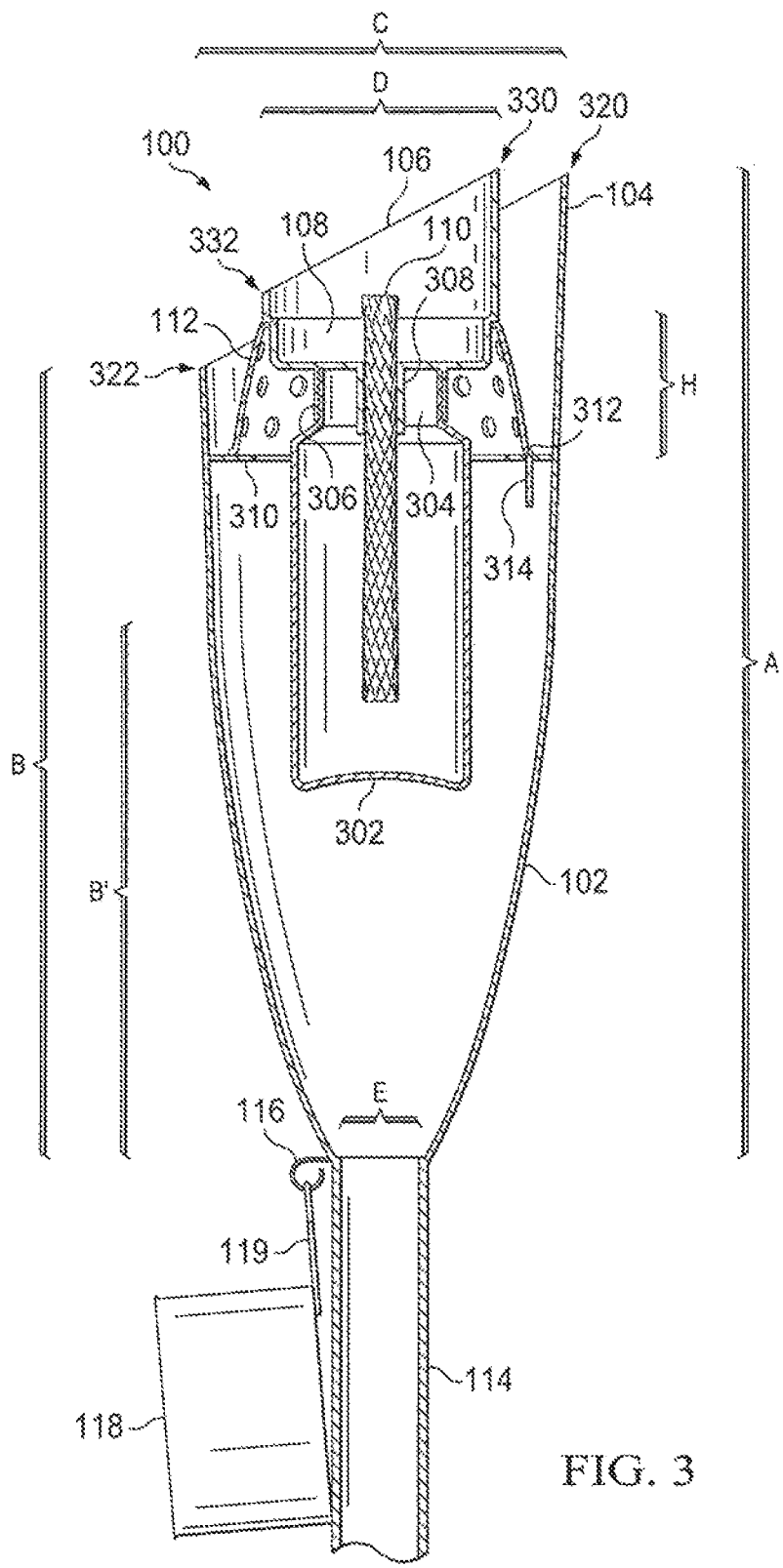
FIG. 3 is a side cutaway view of the torch of FIG. 1.

Referring now to FIG. 3, a side cutaway view of the torch of FIG. 1 is shown. FIG. 3 illustrates additional componentry within the torch 100 as well as certain dimensions of the particular exemplary embodiment shown. It can be seen that a fuel canister 302 is stored at least partially within the torch body 102. In the present embodiment, the fuel canister 302 has a threaded neck 304 that interfits with a threaded connector 306 on the lower portion of the flame bowl 108. In various embodiments, the canister 302 may contain a supply of liquid torch fuel that may be imbued with other chemicals such as scents or repellants.

The flame bowl 108 can also be seen to provide a wick holder 308 that proceeds partially into the fuel canister 302 when the canister 302 is attached to the flame bowl 108. The perforated support 112 may join the flame bowl 108 and/or inner shroud 106 proximate a seam between the two components. The support 112 supports the inner shroud 106, the flame bowl 108, and the fuel canister 302, each at a predetermined height within the torch body 102 and/or outer shroud 104.

In the present embodiment, a lip 310 is provided on the interior of the torch body 102. The lip 310 provides a surface for engaging or supporting the support 112. In some embodiments, the lip 310 will define a slot or hole 312 at a certain location. A tab 314 that protrudes from the support 112 may interfit with the slot 312 in order to ensure that, when assembled, the components each maintain the proper relationship relative to one another. In the present embodiment, one function of the cooperating slot 312 and tab 314 is to ensure that an uppermost rim 320 of the outer shroud 104 can be easily aligned with an uppermost rim 330 of the inner shroud 106. Likewise, the slot 312 and tab 314 allow for easy alignment of a lowermost rim 322 of the outer shroud 104 with a lowermost rim 332 of the inner shroud 106.

As previously discussed, one result of constructing a liquid fuel burning torch according to the present disclosure is that the surfaces that are likely to be touched by a user can be kept at a relatively safe temperature. In some embodiments, the selection of the materials comprising the torch 100 will play a role. For example, stainless steel has good thermal conductive properties. However, dimensions of the device may also need to be considered in order to ensure isolation and/or dispersion of high temperatures. Therefore, a set of dimensions are given below in conjunction with the embodiment of FIG. 3. These dimensions may be used to produce a device of rolled steel with sufficient heat isolation and temperature dispersion properties to be safe for most users. However, this disclosure is not meant to be limited to the specific materials and dimensions given.

In the embodiment of FIG. 3, the overall height of the torch body 102, including the outer shroud 104, at the highest point is given by length A. In the present embodiment, this length is about 10.75 inches. A length B represents the shortest side of the torch body 102 in combination with the outer shroud 104. The length B in the present embodiment is about 8.75 inches. In the present embodiment, the overall diameter of the torch body 102 near the outer shroud 104 is given by dimension C, which is about 3.75 inches. The diameter of the flame bowl 108 and inner shroud 106 is given by dimension D, which in the present embodiment is about 2.5 inches. In the present example, the height H, of the support 112 is about 1.25 inches. Although the size of the torch body 102 where it attaches to the pole 114, length E, may be less critical to controlling temperature than some of the other dimensions, in the present embodiment it is about 1.5 inches.

Using the dimensions described above with respect to FIG. 3, when a common oil based torch fuel is utilized, the temperature at the rim 320 will be approximately 243° F. However, the temperature at the lower rim 322 of the outer shroud 104 will only be 164° F. Further down the torch body 102 temperatures continue to decrease. For example, in FIG. 3, a dimension B' is given, which is approximately ⅔ of the length of the dimension B. At this location, the temperature of the torch 100 when operating is only about 146° F.

It is understood that the inner shroud 106 is generally not safe for user contact when the torch 100 is, or had recently been, operating. However, the overall design and configuration of the torch 100 is meant, in some respects, to discourage a user from inadvertently touching the relatively hot inner shroud 106.

Figure 4:
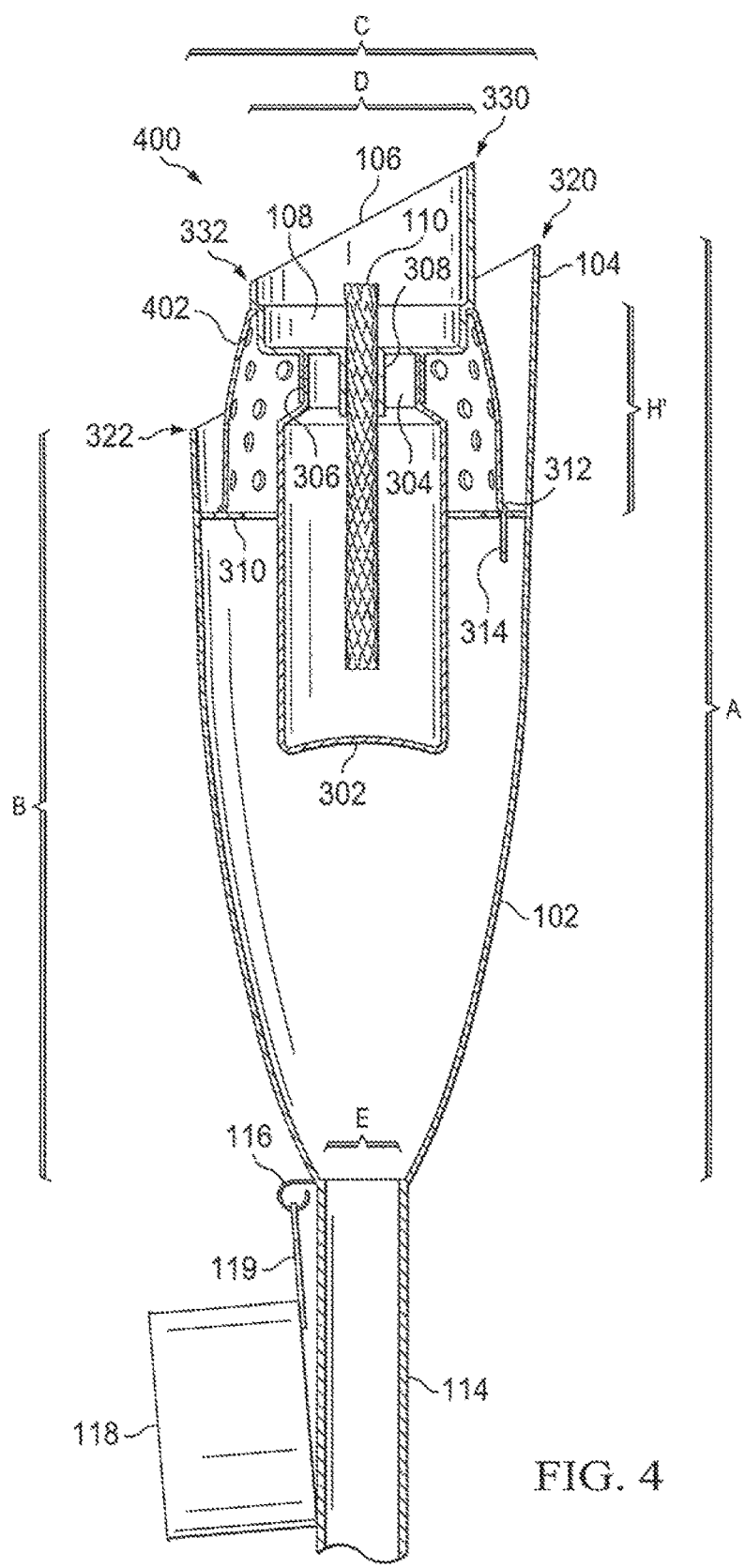
FIG. 4 is a side cutaway view of another embodiment of a heat isolating torch according to the present disclosure.

Referring now to FIG. 4, another embodiment 400 of a heat isolating torch is shown. The embodiment of FIG. 4 is substantially similar to the embodiment of FIG. 3, and shares most components and dimensions. However, in this embodiment, a perforated support 402 having height H' (that is greater than the height H of the support 112) is employed. In the present embodiment, H' is about 1.75 inches. This adjustment of the height of the support 402 elevates the flame bowl 108 at least partially above the level of the outer shroud 104. The inner shroud 106 is elevated substantially above the outer shroud 104. The increase in the height of the support 112 allows for additional heat dissipation from the support 112, as well as providing a longer thermal conductive pathway to the torch body 102. The result of this modification relative to the embodiment of FIG. 3 is that the operating temperature of the upper rim 320 of the outer shroud 104 drops to 176° F. The operating temperature of the lower rim 322 of the outer shroud 104 is approximately 137° F. and decreases along the length B proceeding toward the pole 114.

Figure 5:
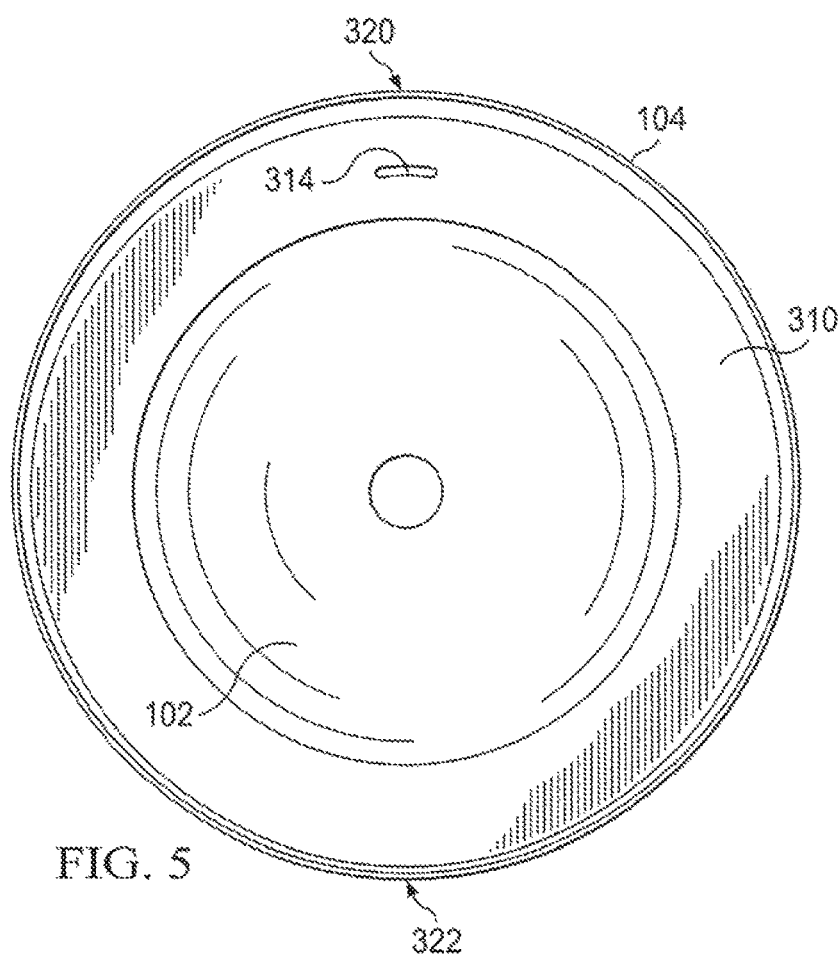
FIG. 5 is a top down view of the shell of the heat isolating torch of FIG. 1.

Referring now to FIG. 5, a top down view of the torch body 102 with the interior components removed is shown. Here, the lip 310 within the torch body 102 can be seen on the interior of the torch body 102. The location of the upper rim 320 and lower rim 322 of the attached outer shroud 104 can also be seen relative to the slot 312 defined in the lip 310.

Figure 6:
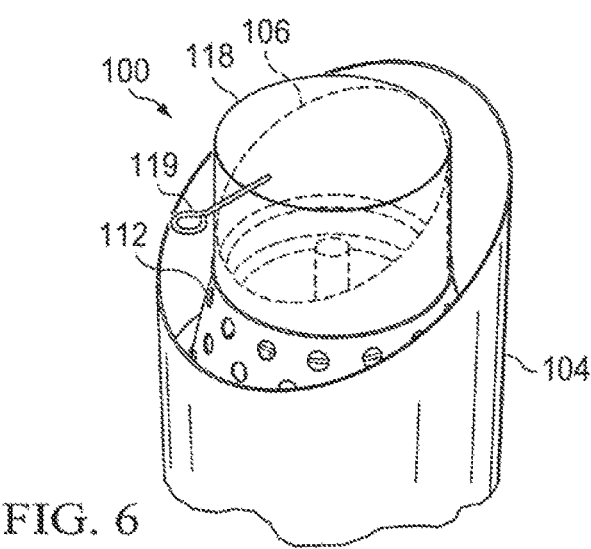
FIG. 6 is a perspective view of the torch of FIG. 1 with the snuffer cap on top.

Referring now to FIG. 6, a perspective view of a portion of the torch 100 is shown. Here, the snuffer cap 118 is shown in place over the inner shroud 106 and the flame bowl 108. It can be seen how the generally cylindrically-shaped snuffer cap 118 will substantially cover and enclose the inner shroud 106. When placed in the configuration shown, the snuffer cap 118 will safely extinguish any flame when the torch 100 is operational. The snuffer cap 118 is provided with a looped handle 119 that may also be used when placing the snuffer cap 118 into the position shown. This will minimize any chance that the user will contact the relatively hot inner shroud 106. Once any flames have been extinguished, the snuffer cap 118 may be removed and replaced on the storage hook 116, possibly using the handle 119.

Figure 7:
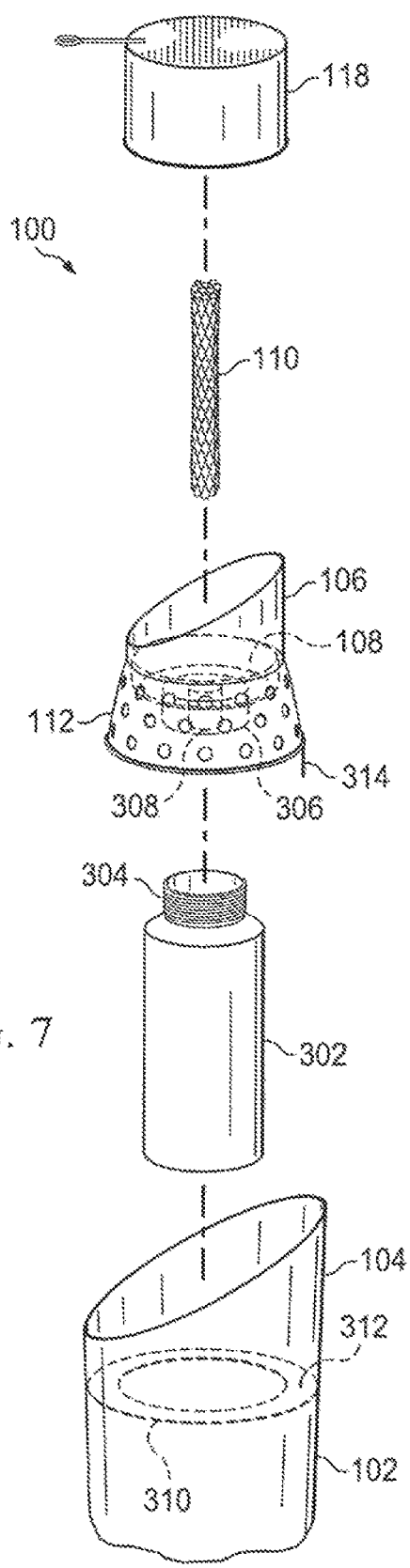
FIG. 7 is an exploded view of the torch of FIG. 1.

Referring now to FIG. 7, an exploded view of the torch 100 is shown. Here, the major components of the torch 100 can be seen separately. When assembling the torch 100, the fuel canister 302 may be attached to the flame bowl 108. The combination of the fuel canister 302, the flame bowl 108, the inner shroud 106, and the support 112 may then be lowered into the torch body 102. The tab 314 may be inserted into the slot 312 to ensure that the outer shroud 104 and inner shroud 106 are in correct alignment relative to one another. The wick 110 may be inserted into the wick holder 308. The wick holder 308 provides a friction fit to retain the wick 110 at the appropriate height. Depending upon the embodiment, the wick 110 may be extended further within the flame bowl 108 to produce greater flame, but at the expense of greater fuel consumption. As previously described, the snuffer cap 118 may be placed over the flame bowl 108 and inner shroud 106 to extinguish an operating torch. When not in use, the cap 118 may be stored on the hook 116.

Figure 8:
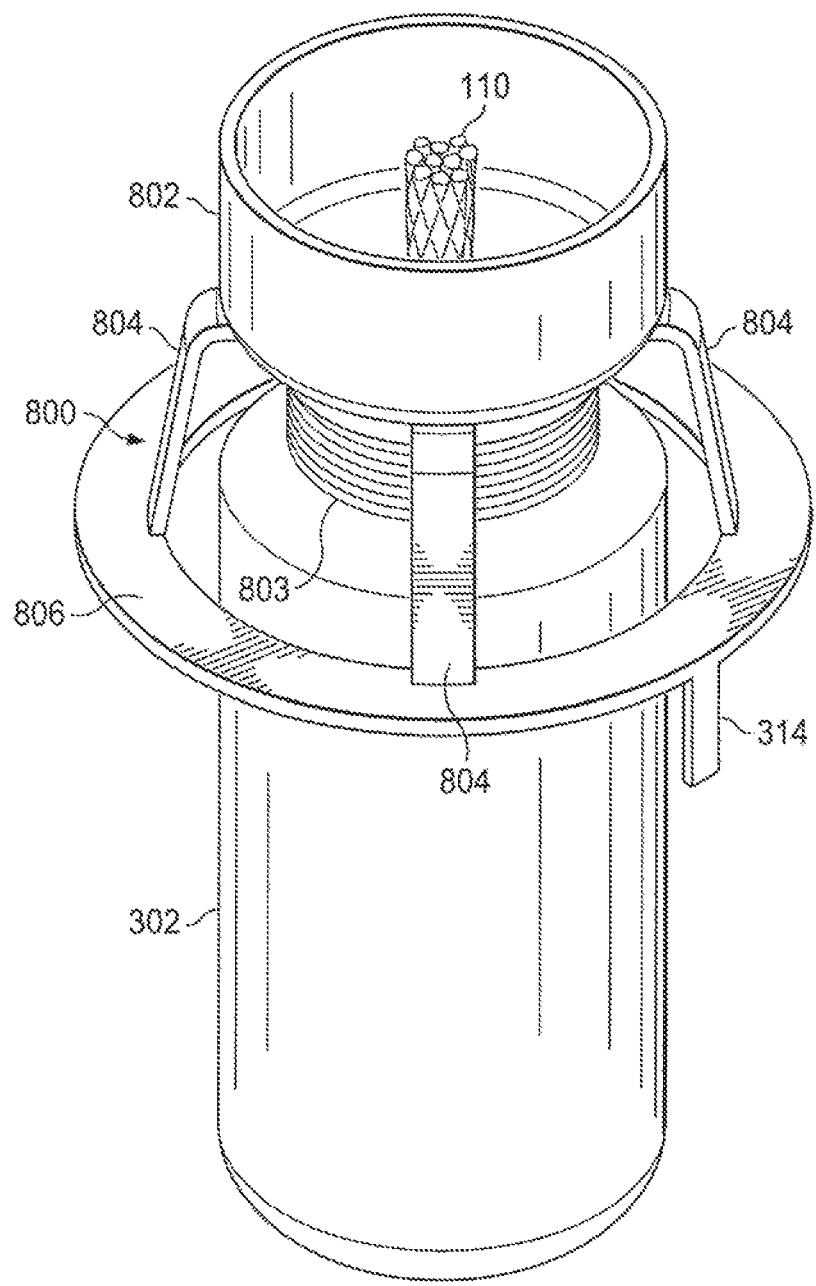
FIG. 8 is a perspective view of a flame bowl support for use with the torch of FIG. 1.

In the previously described embodiments, the supports 112/402 were described as being heat dissipating supports. The supports 112/402, in some embodiments, comprise a metal having a relatively high heat conductance, but also being perforated to dissipate absorbed heat. In other embodiments, an approach may be used to isolate the heat generated in the flame bowl from the rest of the structure. Referring now to FIG. 8, a perspective view of a flame bowl support 800 for use with the torch of FIG. 1 is shown. This support 800 comprises a plurality of legs 804 attached to a ring 806. The ring 806 may sit on the lip 310 (FIG. 3) when the torch 100 is assembled. The ring 806 may also be provided with the tab 314 for fitting into the slot 312 of the lip 310.

In some embodiment, the legs 804 will serve to isolate a flame bowl 802 from the rest of the torch 100. In some embodiments, the legs 804 may be metal, but where additional heat isolation is sought, the legs 804 may comprise a ceramic, resin, or other material having a low thermal conductivity.

The fuel canister 302 is shown attached to a flame bowl 802 via threaded fitting 803. Here the flame bowl 802 is relatively large compared to the wick 110, which may result in a large flame appearance. The flame bowl 802 may comprise the same material as the support 800 or may be made from a different material. In can also be seen that the flame bowl 802 is generally cylindrical in shape rather than having a tapered appearance (e.g., a high side and a low side). It is understood that the tapered appearance of the previously described embodiments is only for illustration, and that inner and outer shrouds and/or flame bowls may have differing appearances than illustrated. In some embodiments, the flame bowl 802 may be textured or coated on an interior thereof to promote a large flame and/or flame effects.

Figure 9A:
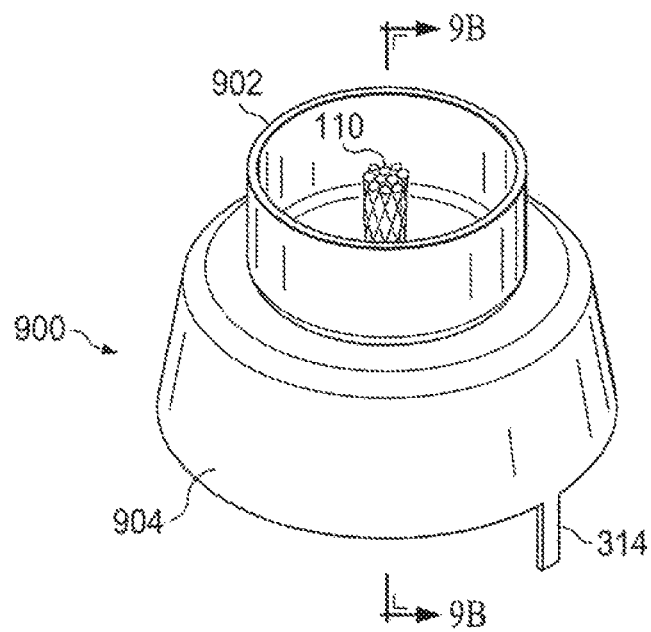
FIG. 9A is a perspective view of another flame bowl support for use with the torch of FIG. 1.

FIG. 9A is a perspective view of another flame bowl support 900 for use with the torch 100 of FIG. 1. Here, the support 900 comprises a non-perforated cone 904 that rests upon a lip 310 (FIG. 3) and supports a flame bowl 902. The support 904 may provide a tab 314 for fitting slot 312. The flame bowl 902 may be generally cylindrical in shape or may have another outline. The cone 904 may comprise a metal, a ceramic, a resin, or another suitable material. In one embodiment, the material for the cone 904 may be chosen for its heat isolation properties.

Figure 9B:
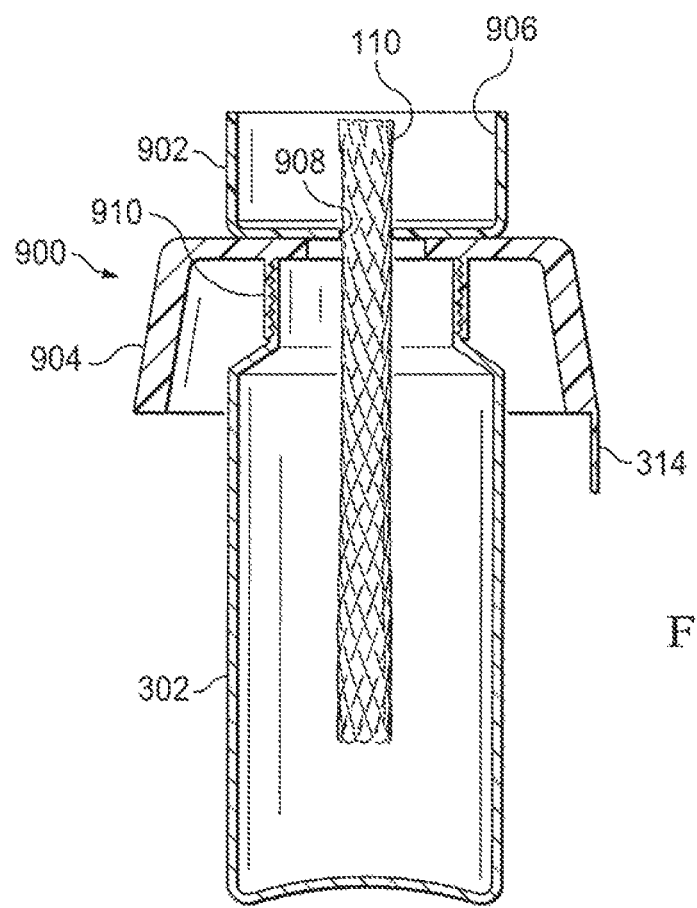
FIG. 9B is a side cutaway view of the support of FIG. 9A.

FIG. 9B is a side cutaway view of the support 900 of FIG. 9A. Here a threaded fitting 910 can be seen. The fitting 910 may be used to attach the fuel reservoir 301 (FIG. 3) to the cone 904 and/or base of the flame bowl 902. The flame bowl 902 may comprise the same material as the support 900, or may comprise a different material. An interior 906 of the flame bowl 902 may be textured or coated to promote a large flame and/or flame effects. A wick holder or wick passage 908 may be defined through the flame bowl 906 and/or support 900 for the wick 110.

Figure 10:
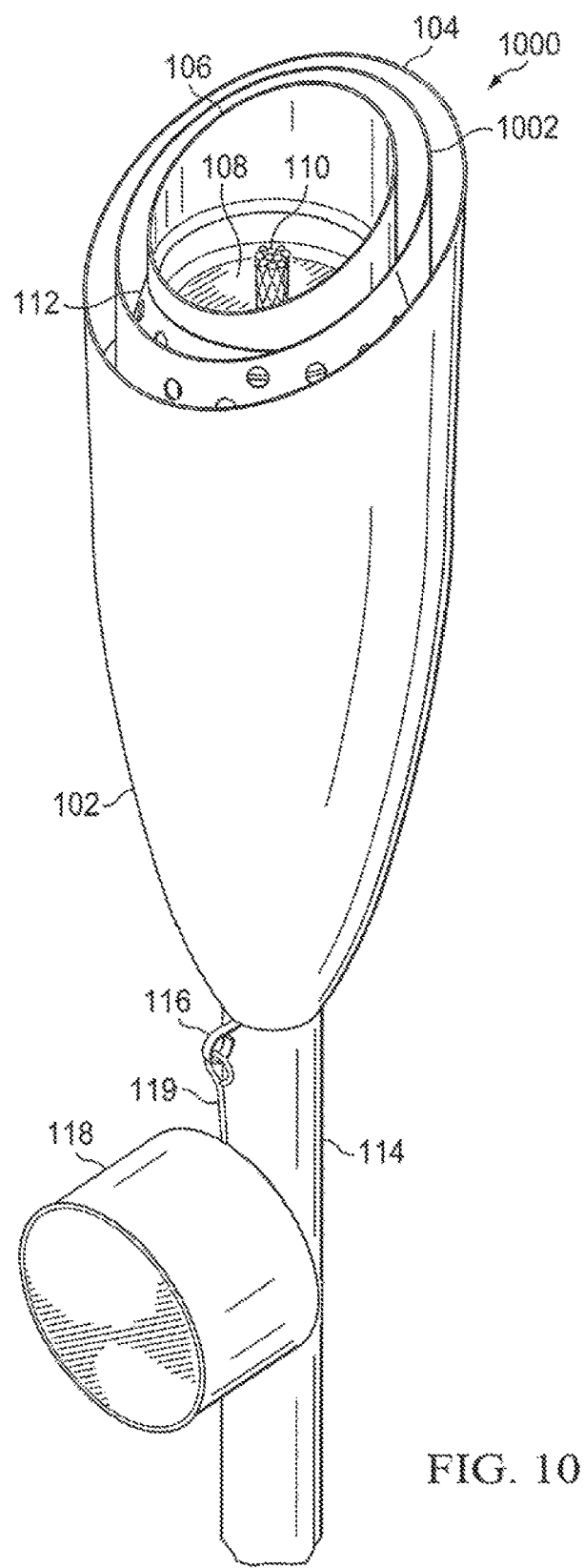
FIG. 10 is a perspective view of another embodiment of a heat isolating torch according to aspects of the present disclosure.

Referring now to FIG. 10, a perspective view of another embodiment of a heat isolating torch according to aspects of the present disclosure is shown. The torch 1000 shares some similarities with the torch 100 of FIGS. 1-7. The torch 1000 has a body 102 that may be cylindrical with a tapered lower portion. The body 102 comprises an outer shroud 104, that may be a continuous portion of the body 102. The torch 100 may also comprise an inner shroud 106 surrounding a flame bowl 108 with a wick 110. The flame bowl 108 and/or an interior portion of the inner shroud 106 may be texturized to promote a large and/or decorative flame from a wick 110. In the present embodiment an intermediate shroud 1002 is situated between the outer shroud 104 and the inner shroud 106. In this configuration the intermediate shroud 1002 surrounds a perforated support 112 that offsets the inner shroud 106 and flame bowl 108 from the body 102 of the torch 1000. The intermediate shroud 1002 may comprise a heat resistant material such as stainless steel.

The torch body 102 may have an attached pole 114 that may be placed in the ground or otherwise affixed to a secure surface. In other embodiments, the torch 100 may be freestanding or configured for placement on a tabletop. A hook 116 may be provided on the body 102, the pole 114, or at the conjunction of the two, as shown. In the present embodiment, the hook 116 is configured to retain a snuffer cap 118, via an attached handle 119, when the snuffer cap 118 is not in use.

Figure 11:
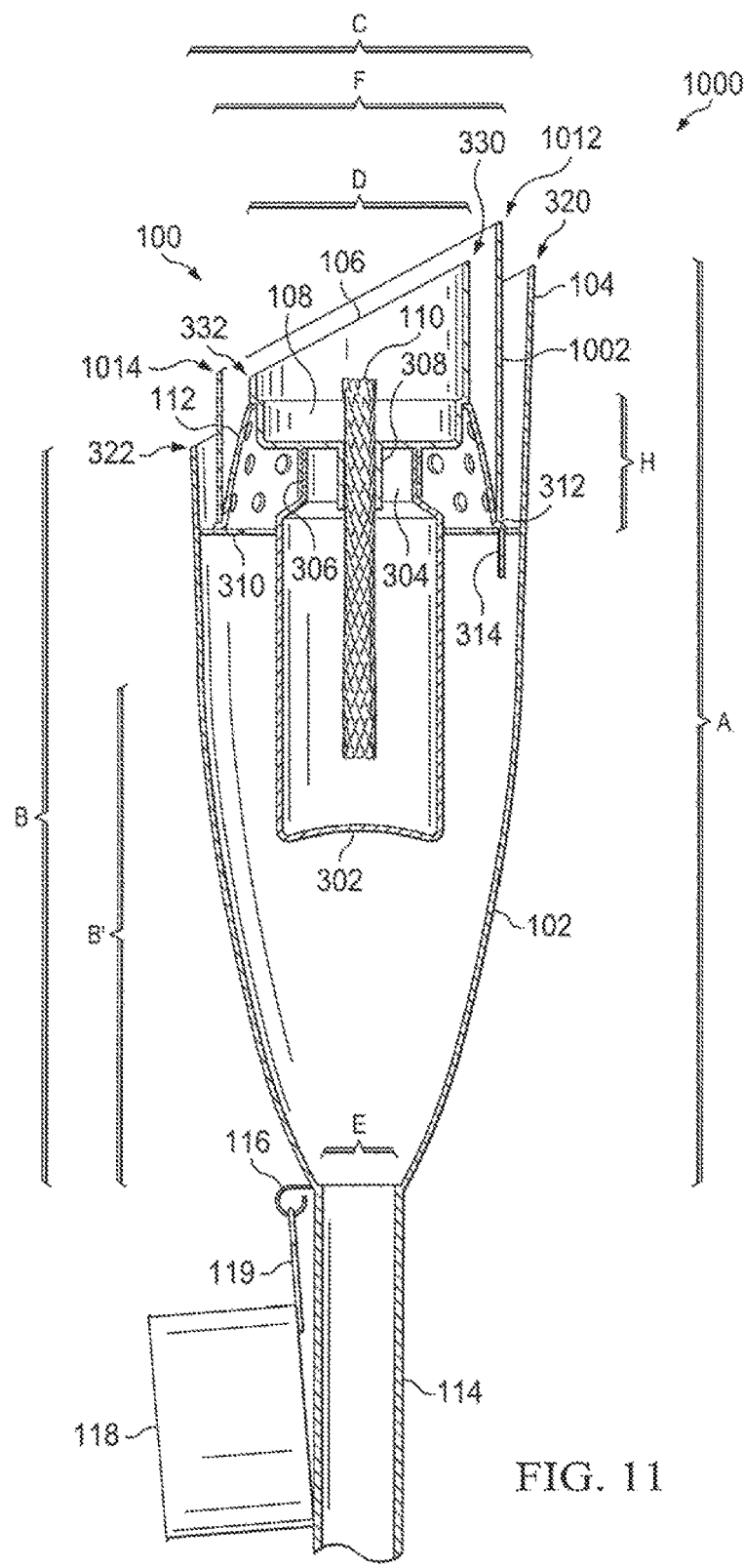
FIG. 11 a side cutaway view of the torch of FIG. 10.

Referring now to FIG. 11, a side cutaway view of the torch 1000 of FIG. 10 is shown. It can be seen that a fuel canister 302 is stored at least partially within the torch body 102. In the present embodiment, the fuel canister 302 has a threaded neck 304 that interfits with a threaded connector 306 on the lower portion of the flame bowl 108. In various embodiments, the canister may contain a supply of liquid torch fuel that may be imbued with other chemicals such as scents or repellants.

The flame bowl 108 can also be seen to provide a wick holder 308 that proceeds partially into the fuel canister 302 when the canister 302 is attached to the flame bowl 108. The perforated support 112 may join the flame bowl 108 and/or inner shroud 106 proximate a seam between the two components. The support 112 supports the inner shroud 106, the flame bowl 108, and the fuel canister 302, each at a predetermined height within the torch body 102 and/or outer shroud 104. The intermediate shroud 1002 can be seen surrounding the support 112 and situated between the outer shroud 104 and inner shroud 106.

In the present embodiment, a lip 310 is provided on the interior of the torch body 102. The lip 310 provides a surface for engaging or supporting the support 112. In some embodiments, the lip 310 will define a slot or hole 312 at a certain location. A tab 314 that protrudes from the support 112 may interfit with the slot 312 in order to ensure that, when assembled, the components each maintain the proper relationship relative to one another. To that end, the intermediate shroud 1002 may be affixed to the support 112.

The intermediate shroud 1002 has an angled outline as seen from the present side view. The shroud 1002 may have an uppermost rim 1012 and a lowermost rim 1014. These will correspond to the uppermost rim 330 and lowermost rim 332 of the inner shroud 106, respectively. Furthermore, the cooperating slot 312 and tab 314 may ensure the uppermost rim 320 of the outer shroud 104 can be easily aligned with an uppermost rim 330 of the inner shroud 106. Likewise, the slot 312 and tab 314 allow for easy alignment of the lowermost rim 322 of the outer shroud 104 with a lowermost rim 332 of the inner shroud 106. Hence, all upper and lower rims will be in alignment.

The dimensions of the torch 1000 may vary from, or be the same as, those of the torch 100 of FIG. 1. Various dimensions are listed here again. The overall height of the torch body 102, including the shroud 104, at the highest point is given by length A. A length B represents the shortest side of the torch body 102 in combination with the outer shroud 104. The overall diameter of the torch body 102 near the outer shroud 104 is given by dimension C. The diameter of the flame bowl 108 and inner shroud 106 is given by dimension D. H is the height of the support 112. The size of the torch body 102 where it attaches to the pole 114 is length E. In addition to these dimension shared with the torch 100, the torch 1000 also has a width F of the shroud 1002, which will have a value somewhere between lengths C and D.

The height of the shroud 1012, as measured from the lip 310 to the uppermost rim 1012 or lowermost rim 1014, is variable. In some embodiments the shroud 1002 is not angled but is relatively flat (with rims 1012, 1014 of roughly the same height). In such cases, the height of the shroud 1002 will roughly match the height H of the support 112. In other embodiments, the shroud may remain of level height but be taller than the support 112. In cases where the shroud 1002 is angled, it may be taller or shorter than the inner shroud 106 or outer shroud 104. In some embodiments, the height of the shroud 1002 falls between the shrouds 104, 106.

It will be appreciated that, in various embodiments, the shrouds 104, 106, 1002, the torch body 102, the flame bowl 108, and the wick 110 are arranged in a concentric, or circumscribing arrangement. For example, the support 112 may be said to circumscribe, or surround, at least a portion of the flame bowl 108, which circumscribes the wick 110. It may be said that the inner shroud 106 circumscribes the flame bowl 108 even though they are not always on the same horizontal plane. The intermediate shroud 1102 circumscribes all or a portion of the support and inner shroud 106. The intermediate shroud 1002 may be circumscribed by all or a portion of the outer shroud 104 and/or the torch body 102.

It is understood that the inner shroud 106 is generally not safe for user contact when the torch 1000 is, or had recently been, operating. However, the overall design and configuration of the torch 1000 is meant, in some respects, to discourage a user from inadvertently touching the relatively hot inner shroud 106. In the present embodiment, the intermediate shroud 1002 provides and additional barrier against radiative conductivity of heat from the inner shroud 106 and flame bowl 108 to the outer shroud 104 and or torch body 100. In addition, the extent the intermediate shroud 1002 becomes heated, the heat will be transferred to the lip 310, and only indirectly to a surface 102 of the torch body 102.

The support 112 provides perforations that both assist in dispersing heat into the air, and in promoting cooling airflow in and around the flame bowl 108. In some embodiments, the shrouds 104, 106, 1002 may be relatively small, or even non-existent. Such embodiments rely solely on the support 112 to provide adequate cooling for the flame bowl 108. The general shape of the support may be frustroconical. In some embodiments, a lower portion of the support 112 will be wider (have a larger radius) that an upper portion. The perforations of the support 112 may be circular and formed by punching through the side of the support 112. They may also be square, or have other shapes that reduce the amount of mass available in the support 112 to conduct heat while increasing the air flow through the support 112.

Figure 16A:
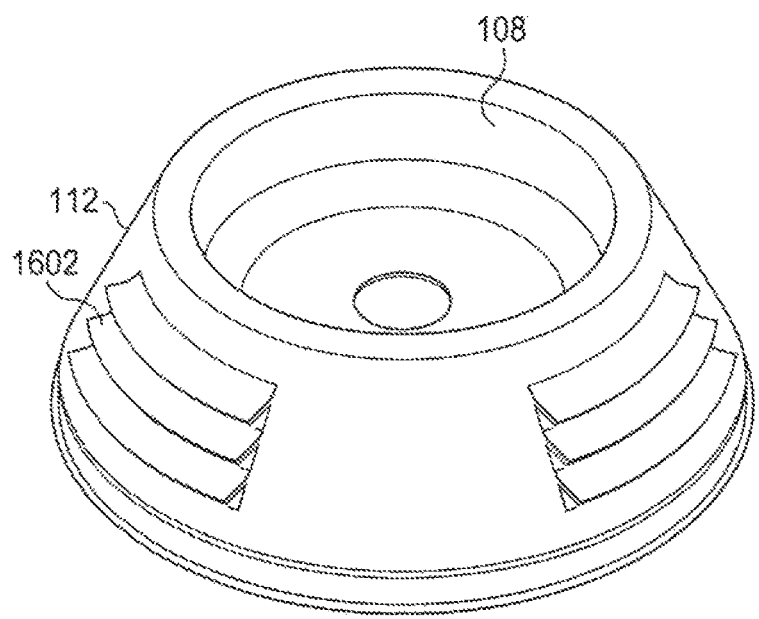
FIG. 16A is a perspective view of another embodiment of a perforated support for use with torches of the present disclosure.
Figure 16B:
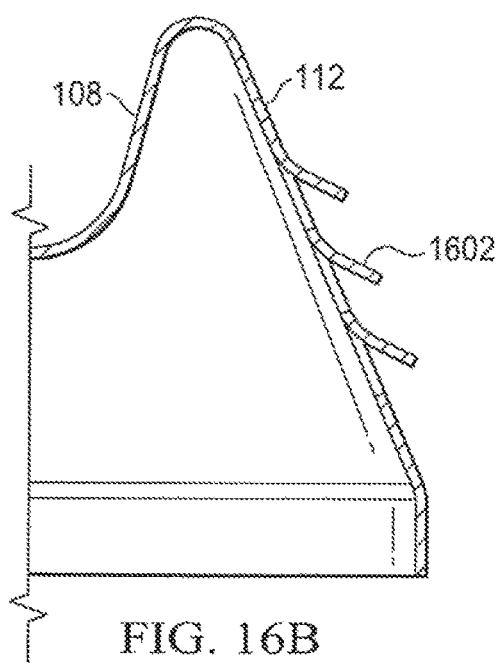
FIG. 16B is a partial side cutaway view of the perforated support of FIG. 16A.

Referring now to FIG. 16A, some embodiments may have a support 112 provided with louvers 1602 instead of, or in addition to, perforations. Louvers do not necessarily remove material from the support 112 but do restrict the available thermal conductive pathways while promoting air flow. Furthermore, the louvers are not configured exactly as shown in all embodiments. FIG. 16B illustrates the support of FIG. 16A in a partial side cutaway view.

Figure 15:
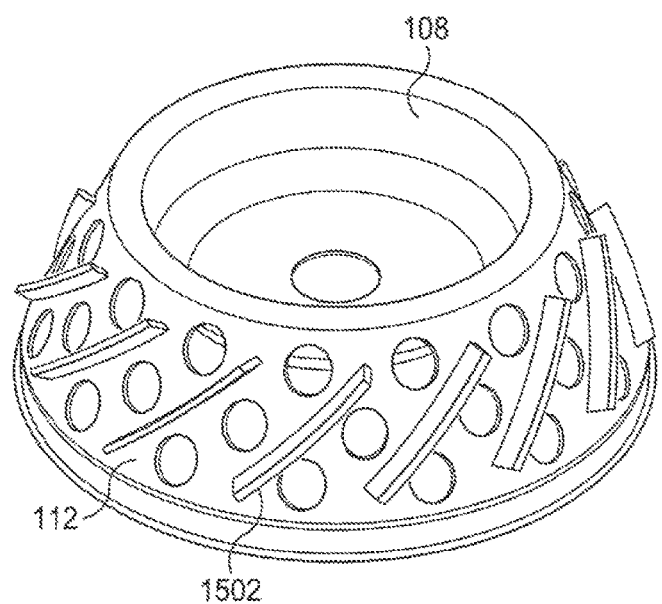
FIG. 15 is a perspective view of one embodiment of perforated support for use with torches of the present disclosure.

Referring now to FIG. 15, the support 112 may have a series of radiative fins 1502 that increase heat dispersal (though the fins are not necessarily configured as shown). Again, these may be in addition to, or instead of, perforations.

Figure 12:
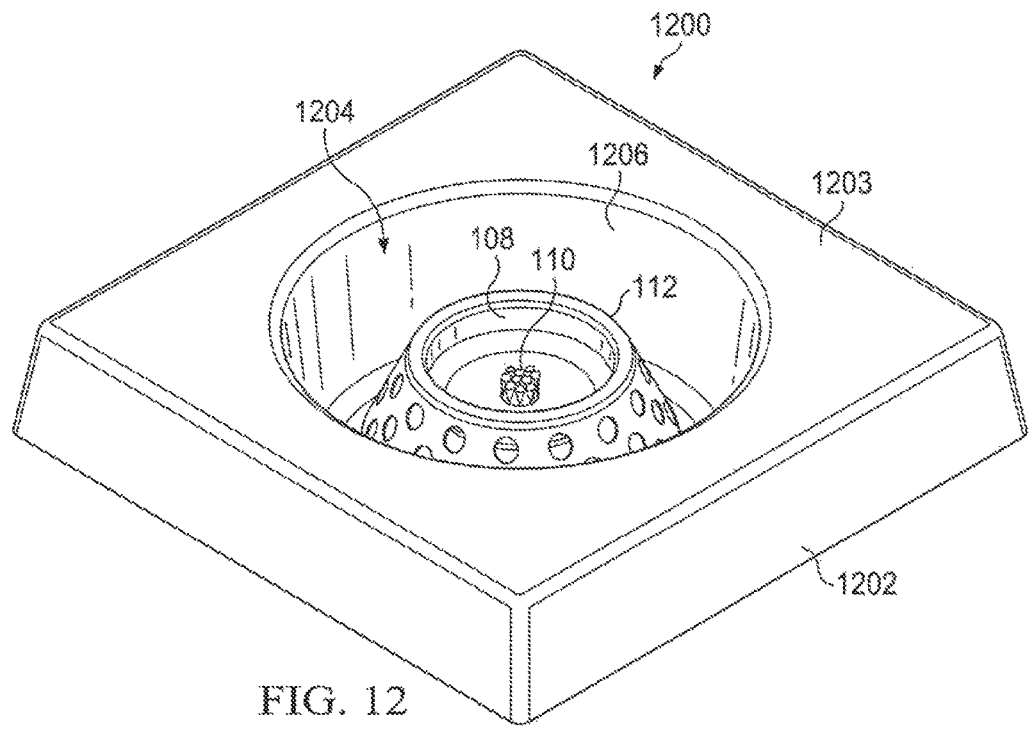
FIG. 12 is a perspective view of another embodiment of a heat isolating torch according to aspects of the present disclosure.

Referring now to FIG. 12, a perspective view of another embodiment of a heat isolating torch according to aspects of the present disclosure is shown. The torch 1200 provides a top 1202 that may affix to a separate stand (not shown) and provide for burning of a liquid fuel. A large flame bowl 108 is fitted within a recess 1204 in an upper surface 1203 of the top 1202. The flame bowl provides a wick 110 and may be texturized on an inner surface thereof to promote a larger flame and enhanced flame effects. An inner side wall 1206 may provide support for the fire bowl 108. In the present embodiment, the firebowl 108 is attached to the side wall 1206 via a support 112. As in previous embodiments, the support 112 may be perforated to limit heat transfer from the firebowl 108 to the sidewall 1206 and top 1202, and to promote cooling air flow.

It will be appreciated that, in the present embodiment, the top 1202 in general, and the side wall 1206 in particular, act as a shroud to both contain and isolate heat from the flame bowl 108. The aforementioned perforated support 112 also aids in this regard. The top 1202 may comprise a stainless steel, a coated or painted metal, or another heat resistant, and possibly decorative, construction.

Figure 13:
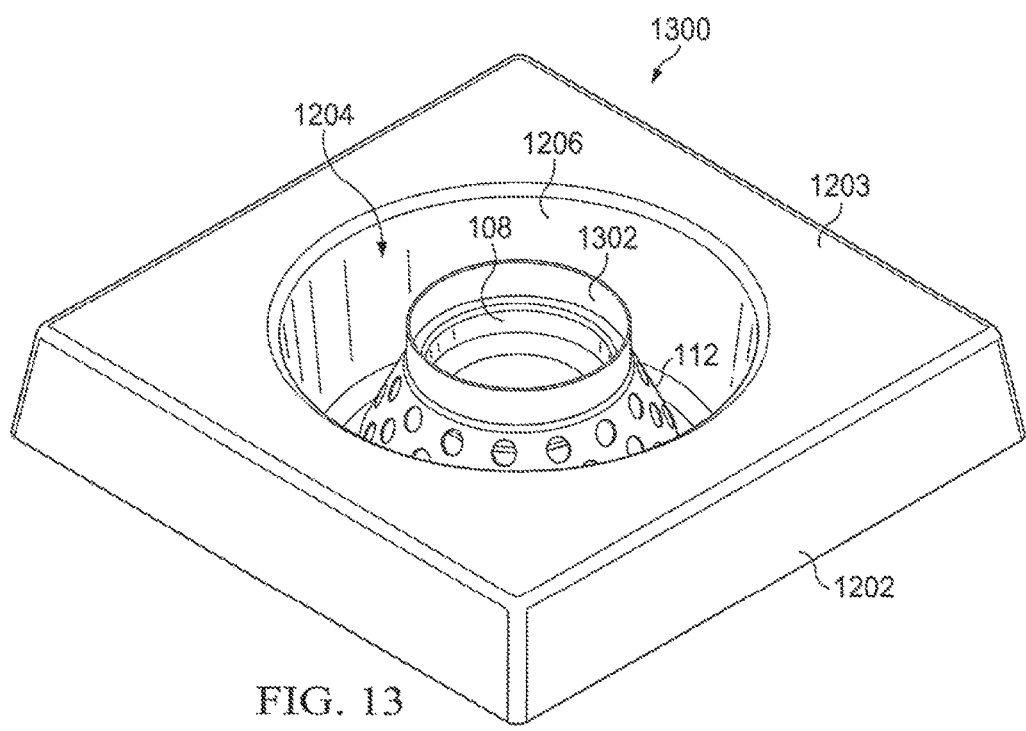
FIG. 13 is a perspective view of another embodiment of a heat isolating torch according to aspects of the present disclosure.

Referring now to FIG. 13, a perspective view of another embodiment of a heat isolating torch according to aspects of the present disclosure. The torch 1300 is substantially similar to the torch 1200 but or the addition of an internal shroud 1302. The internal shroud 1302, in the present embodiment, affixes to an outer periphery of the fire bowl 108 atop the support 112. The shroud 1302 provides further isolation of heat and flame from the recess 1204 and sidewall 1206. In this regard, the torch 1300 may be considered to be a double shrouded design with the inner shroud 1302 surrounded by the sidewall 1206 and top 1202 acting as a second shroud.

Figure 14:
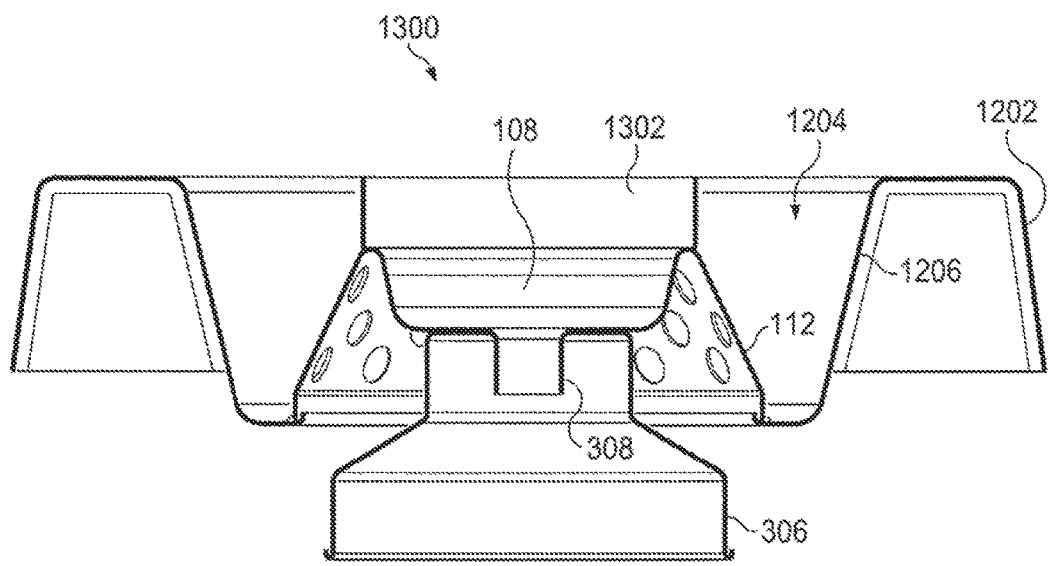
FIG. 14 is a side cutaway view of the torch of FIG. 13.

Referring now to FIG. 14, a side cutaway view of the torch 1300 of FIG. 13 is shown. From this view it can be appreciated that the side wall 1206 descends from an upper surface of the top 1202 forming recess 1204. A portion of the sidewall 1206 extends to meet the support 112 which affixes the flame bowl 108 into position. In the present embodiment, the shroud 1302 is generally cylindrical in outline and joins to the flame bowl 108 and/or support 112 and extends upward. As with previous embodiments, the flame bowl provides a fitting which holder 308 and a fuel bottle fitting 306. The fitting 306 may be threaded for attaching to a threaded fuel supply (not shown) or may provide a snap on or interference type fit. It will be appreciated the perforated support 112 allows less heat to be transferred from the flame bowl to the top 1202 of the torch 1300 by virtue of providing a reduced thermal conductivity path versus that present of the support 112 were solid. Further the perforated support 112 allows for cooling air and convection currents around and underneath the bowl 108 and top 1202.

Figure 17:
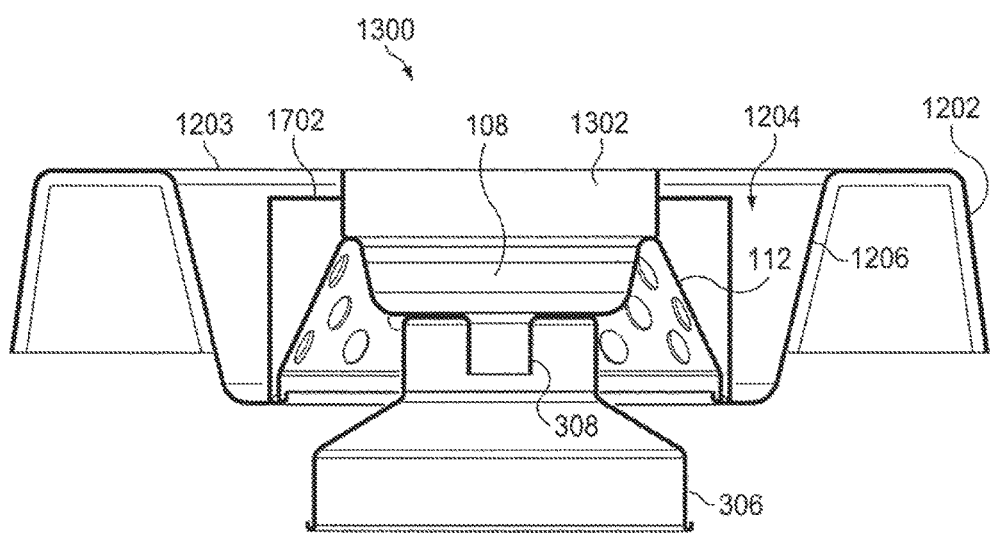
FIG. 17 is a side cutaway view of another embodiment of a heat isolating torch according to aspects of the present disclosure.

Referring now to FIG. 17 a side cutaway view of another embodiment of a heat isolating torch according to aspects of the present disclosure is shown. The embodiment of FIG. 17 is substantially similar to the embodiment of FIGS. 13-14 with the addition of an intermediate shroud 1702. The shroud 1702 may proceed upward from the recess 1204 and circumscribe the support 112 and inner shroud 1302. The shroud 1702 may join to the sidewall 1206 near where it proceed inwardly to attach to the support 112, or it may attach to the support 112 itself near the lower, wider portion. The height of the shroud 1702 may vary and it may or may not protrude above the level of the shroud 1302 or the upper surface 1203.

Thus, the present invention is well adapted to carry out the objectives and attain the ends and advantages mentioned above as well as those inherent therein. While presently preferred embodiments have been described for purposes of this disclosure, numerous changes and modifications will be apparent to those of ordinary skill in the art. Such changes and modifications are encompassed within the spirit of this invention as defined by the claims.

What is claimed is:

1. A device comprising:
   a torch top having a recess in an upper surface thereof;
   a sidewall descending from the upper surface into the recess;
   a flame bowl providing a wick holder; and
   a conic, perforated support that extends upwardly and inwardly from the sidewall and retains the flame bowl at a fixed position within the recess and entirely below the upper surface and provides a plurality of perforations allowing convection currents therethrough and underneath the flame bowl providing the wick holder.

2. The device of claim 1, further comprising a first shroud attached to the flame bowl and circumscribing the wick holder.

3. The device of claim 2, further comprising a second shroud at least partially within the recess and circumscribing the first shroud.

4. The device of claim 2, further comprising a fuel container fitting affixed to the flame bowl and at least partially circumscribed by the perforated support.

5. The device of claim 1, wherein a lower portion of the sidewall extends inwardly to attach to the perforated support.

6. A device comprising:
   a top having an upper surface;
   a sidewall descending from the upper surface to define a recess;
   a conic perforated support extending upwardly from the sidewall into the recess;
   a textured flame bowl defining a liquid fuel burning wick holder for a torch having a torch body containing a liquid fuel supply; and
   a fitting attached to the flame bowl for interfacing with the fuel supply;
   wherein the conic perforated support elevates the flame bowl within the recess toward the upper surface but the flame bowl remains below the upper surface; and
   wherein the conic perforated support defines a plurality of perforations that allow for fluid communication of air underneath the flame bowl.

7. The device of claim 6, further comprising a first shroud circumscribing the flame bowl.

8. The device of claim 7, further comprising a second shroud circumscribing the first shroud, the flame bowl, and the perforated support.

9. The device of claim 6, wherein the perforated support has a smaller radius proximate the flame bowl and a larger radius spaced apart from the flame bowl.

10. The device of claim 6, further comprising a shroud circumscribing the flame bowl at a level proximate the upper surface.

11. A device comprising:
    an upwardly concave flame bowl defining a liquid fuel wick holder;
    a first, inner shroud affixed to the flame bowl and extending upwardly therefrom circumscribing the wick holder;
    a shell having a second, outer shroud on an upper portion thereof, the outer shroud circumscribing at least a portion of the first, inner shroud;
    an upwardly extending, conic, perforated support having a lower end wider than an upper end, maintaining the flame bowl and the first shroud in a fixed relationship with respect to the second, outer shroud, and suspending a fuel canister affixed to the flame bowl within the shell; and a third, intermediate shroud circumscribing the perforated support and interposing the first and second shrouds;

wherein the upwardly extending, conic, perforated support maintains the flame bowl, exclusive of the first, inner shroud, entirely below a level of the second, outer shroud; and wherein the perforated support defines a plurality of perforations below a level of the flame bowl and the plurality of perforations are at or below a level of the second, outer shroud.

12. The device of claim 11, further comprising a lip in the shell that supports the perforated support in a predetermined position inside the shell.

13. The device of claim 11, wherein each of the first, inner shroud, the second, outer shroud, and the third, intermediate shroud has an angled profile with an upper rim and a lower rim.

* * * * *